(12) United States Patent
Tanaka et al.

(10) Patent No.: US 10,092,248 B2
(45) Date of Patent: Oct. 9, 2018

(54) VITAL SIGNS MEASURING APPARATUS, VITAL SIGNS DISPLAYING METHOD, AND PROGRAM

(71) Applicant: NIHON KOHDEN CORPORATION, Tokyo (JP)

(72) Inventors: Takayuki Tanaka, Tokyo (JP); Yuko Ishinabe, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 14/887,516

(22) Filed: Oct. 20, 2015

(65) Prior Publication Data

US 2016/0113593 A1   Apr. 28, 2016

(30) Foreign Application Priority Data

Oct. 21, 2014 (JP) .................................. 2014-214152

(51) Int. Cl.
*A61B 5/00* (2006.01)
*A61B 5/145* (2006.01)
(Continued)

(52) U.S. Cl.
CPC ................ *A61B 5/742* (2013.01); *A61B 5/01* (2013.01); *A61B 5/021* (2013.01); *A61B 5/024* (2013.01);
(Continued)

(58) Field of Classification Search
CPC .. A61N 1/3962; A61N 1/3622; A61N 1/3621; A61N 1/395; A61N 1/3956
See application file for complete search history.

(56) References Cited

U.S. PATENT DOCUMENTS 5,305,745 A * 4/1994 Zacouto ................. A61B 5/046
600/324
5,578,063 A * 11/1996 Bocek ................. A61N 1/37247
607/5
(Continued)

FOREIGN PATENT DOCUMENTS

EP    1 637 070 A2    3/2006
EP    2 778 883 A2    9/2014
(Continued)

OTHER PUBLICATIONS

Partial European Search Report issued in Patent Application No. EP 15 19 0758 dated Oct. 9, 2017.
(Continued)

*Primary Examiner* — Todd Buttram
(74) *Attorney, Agent, or Firm* — Pearne & Gordon LLP

(57) ABSTRACT

A vital signs measuring apparatus includes: a measuring section which is configured to measure vital signs of a subject; a receiving section which is configured to receive vital signs of the subject transmitted from a source measuring apparatus; a displaying section which is configured to display at least one of the vital signs measured by the measuring section, and the vital signs received by the receiving section; and a controlling section which is configured to produce a display screen that is to be displayed on the displaying section, the controlling section which is configured to change a display effect of vital signs on the display screen, based on whether the vital signs are received by the receiving section or not.

15 Claims, 10 Drawing Sheets

(51) Int. Cl.
  *A61B 5/01* (2006.01)
  *A61B 5/0402* (2006.01)
  *A61B 5/021* (2006.01)
  *A61B 5/024* (2006.01)
  *G16H 40/63* (2018.01)
  *G06F 19/00* (2018.01)

(52) U.S. Cl.
  CPC ........ *A61B 5/0402* (2013.01); *A61B 5/14542* (2013.01); *G06F 19/00* (2013.01); *G16H 40/63* (2018.01)

(56) References Cited

U.S. PATENT DOCUMENTS

| | | | | |
|---|---|---|---|---|
| 5,764,214 | A * | 6/1998 | Takano | G09G 5/14 345/619 |
| 7,769,465 | B2 * | 8/2010 | Matos | A61N 1/0476 607/1 |
| 9,377,485 | B2 * | 6/2016 | Epperson | G01R 1/025 |
| 9,478,045 | B1 * | 10/2016 | Hunnicutt | G06F 1/163 |
| 2002/0099274 | A1 * | 7/2002 | Isomura | A61B 5/0002 600/300 |
| 2004/0122476 | A1 * | 6/2004 | Wung | A61B 5/044 607/5 |
| 2004/0204743 | A1 * | 10/2004 | McGrath | A61N 1/08 607/5 |
| 2005/0075839 | A1 * | 4/2005 | Rotheroe | G05B 23/0272 702/183 |
| 2008/0171311 | A1 * | 7/2008 | Centen | G09B 23/288 434/265 |
| 2010/0094147 | A1 | 4/2010 | Inan et al. | |
| 2011/0202100 | A1 * | 8/2011 | Tan | A61H 31/005 607/6 |
| 2012/0108917 | A1 * | 5/2012 | Libbus | A61B 5/0006 600/301 |
| 2012/0259179 | A1 | 10/2012 | Sullivan et al. | |
| 2015/0005609 | A1 * | 1/2015 | Evans | A61B 5/0006 600/384 |
| 2015/0079560 | A1 * | 3/2015 | Cowan | A61B 5/742 434/236 |
| 2015/0220262 | A1 * | 8/2015 | Patel | G06F 3/04847 715/863 |
| 2015/0339792 | A1 | 11/2015 | Emori et al. | |
| 2016/0030758 | A1 * | 2/2016 | Guiney | A61N 1/3925 607/5 |
| 2016/0059024 | A1 * | 3/2016 | Stahmann | A61N 1/3702 607/4 |
| 2016/0331260 | A1 * | 11/2016 | Han | A61B 5/0468 |

FOREIGN PATENT DOCUMENTS

| | | |
|---|---|---|
| JP | 2009-139624 A | 6/2009 |
| JP | 2009-189443 A | 8/2009 |
| JP | 2011-078640 A | 4/2011 |
| JP | 2014-61181 A | 4/2014 |
| JP | 2014147486 A * | 8/2014 |
| JP | 2014-170263 A | 9/2014 |
| WO | 2007-076435 A2 | 7/2007 |
| WO | 2011-100534 A1 | 8/2011 |
| WO | 2013-056160 A2 | 4/2013 |
| WO | 2013-169297 A1 | 11/2013 |

OTHER PUBLICATIONS

Japanese Office Action issued in Patent Application No. JP-2014-214152 dated Nov. 21, 2017.
Extended European Search Report issued in Patent Application No. EP 15 19 0758.1 dated Feb. 12, 2018.

* cited by examiner

FIG. 6

```
<Apparatus information>

<Use>transportation</Use>
    <Apparatus ID>tr-111</Apparatus ID>
    <Apparatus type>Life Scope XXX</Apparatus type>

</Apparatus information>
```

FIG. 7A

| RECEIVED BY RECEIVING SECTION 130 | USE | DISPLAY EFFECT |
|---|---|---|
| ○ | TRANSPORTATION | BACKGROUND COLOR = GRAY |
| ○ | EQUIPPED IN AMBULANCE | BACKGROUND COLOR = GREEN |
| ○ | BEDSIDE | BACKGROUND COLOR = BLACK |
| × | BEDSIDE | BACKGROUND COLOR = BLACK |
| ○ | — | BACKGROUND COLOR = GRAY |

FIG. 7B

| USE | DISPLAY EFFECT |
|---|---|
| TRANSPORTATION | BACKGROUND COLOR = GRAY |
| EQUIPPED IN AMBULANCE | BACKGROUND COLOR = GREEN |
| BEDSIDE | BACKGROUND COLOR = BLACK |
| — ("MEASURED BY OWN APPARATUS") | BACKGROUND COLOR = DEEP BLUE |

VITAL SIGNS MEASURING APPARATUS, VITAL SIGNS DISPLAYING METHOD, AND PROGRAM

CROSS-REFERENCE TO RELATED APPLICATION(S)

This application is based upon and claims the benefit of priority from prior Japanese patent application No. 2014-214152, filed on Oct. 21, 2014, the entire contents of which are incorporated herein by reference.

BACKGROUND

The presently disclosed subject matter relates to a vital signs measuring apparatus, a vital signs displaying method, and a program.

Various kinds of vital signs measuring apparatuses for measuring vital signs (an electrocardiogram, respiration, the body temperature, and the like) of the patient have been developed. As a vital signs measuring apparatus, for example, a so-called bedside monitor, a transport monitor, a defibrillator, a telemeter, and the like are known.

In such vital signs measuring apparatuses, measurement conditions are largely different depending on apparatuses. For example, a bedside monitor is placed mainly in a ward of a hospital, and measures vital signs of the patient without moving. By contrast, a transport monitor is often used in, for example, patient transportation using a bed (namely, in a moving state). A defibrillator is used often in a surgery room or the like, or equipped in an ambulance or the like.

Preferably, the display screen of such a vital signs measuring apparatus is configured so that the condition (measurement values and waveforms of various parameters) of the patient is conveyed in an easy understanding manner to the user (mainly the doctor or the nurse). Hereinafter, the related art of the screen display in a vital signs measuring apparatus will be described.

For example, JP-A-2014-61181 discloses a technique for differentiating a background color of an image relating to an electrocardiogram measurement from that of an image relating to a blood pressure pulse wave. JP-A-2009-139624 discloses an image diagnostic apparatus which is used for an X-ray CT or ultrasonic diagnosis, and in which the color tone is changed in accordance with the imaging mode.

As described above, there are many kinds of vital signs measuring apparatuses. Therefore, measurement values and waveforms are different in correctness depending on the measurement conditions. Considering values (an electrocardiogram and the like) of various parameters which are measured by using a transport monitor during movement, and values (an electrocardiogram and the like) of various parameters which are measured by using a bedside monitor during patient rest time, for example, the latter values are usually higher in measurement accuracy.

Networking or the like of vital signs measuring apparatuses has been advanced, and it is possible to use measurement values and waveforms which are measured by another vital signs measuring apparatus. In a vital signs measuring apparatus, therefore, a situation may be possible where vital signs which are measured in a motionless state, and those which are measured in a motion state are mixed on the same display screen. A further situation may be possible where the measurement accuracy of vital signs is different in accordance with whether the vital signs measuring apparatus is of a sophisticated type or of a general-purpose type. In this case, preferably, the user of the vital signs measuring apparatus can know not only measurement values and waveforms, but also measurement conditions (such as the type of the measuring apparatus, the vibration condition, the function of the measuring apparatus, and the measurement environment (whether measurement is performed outdoors or not)).

However, the existing techniques including the techniques disclosed in JP-A-2014-61181 and JP-A-2009-139624 suggest or teach nothing about a technique in which vital signs are referenced after recognizing measurement conditions. Namely, vital signs cannot be referred after recognizing measurement conditions, and hence there is a problem in that the user may perform erroneous diagnosis.

SUMMARY

The presently disclosed subject matter may provide a vital signs measuring apparatus, vital signs displaying method, and program in which vital signs can be referred after recognizing measurement conditions.

The vital signs measuring apparatus may comprise: a measuring section which is configured to measure vital signs of a subject; a receiving section which is configured to receive vital signs of the subject transmitted from a source measuring apparatus; a displaying section which is configured to display at least one of the vital signs measured by the measuring section, and the vital signs received by the receiving section; and a controlling section which is configured to produce a display screen that is to be displayed on the displaying section, the controlling section which is configured to change a display effect of vital signs on the display screen, based on whether the vital signs are the vital signs received by the receiving section or not.

BRIEF DESCRIPTION OF THE DRAWINGS

FIG. 6 is a view showing an example of attribute data in Embodiment 2.

FIGS. 7A and 7B are views showing a correlation table in Embodiment 2.

DETAILED DESCRIPTION OF EXEMPLARY EMBODIMENTS

Embodiment 1

Figure 1:
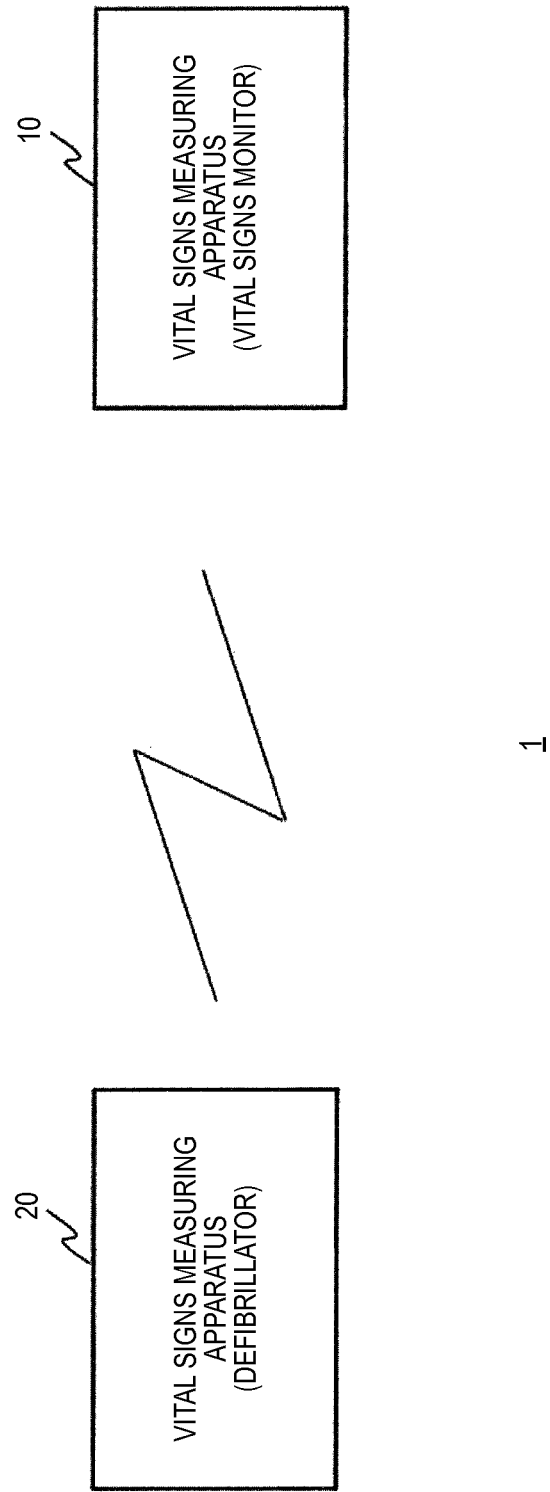
FIG. 1 is a block diagram showing the configuration of a vital signs measuring system 1 of Embodiment 1.
Figure 2:
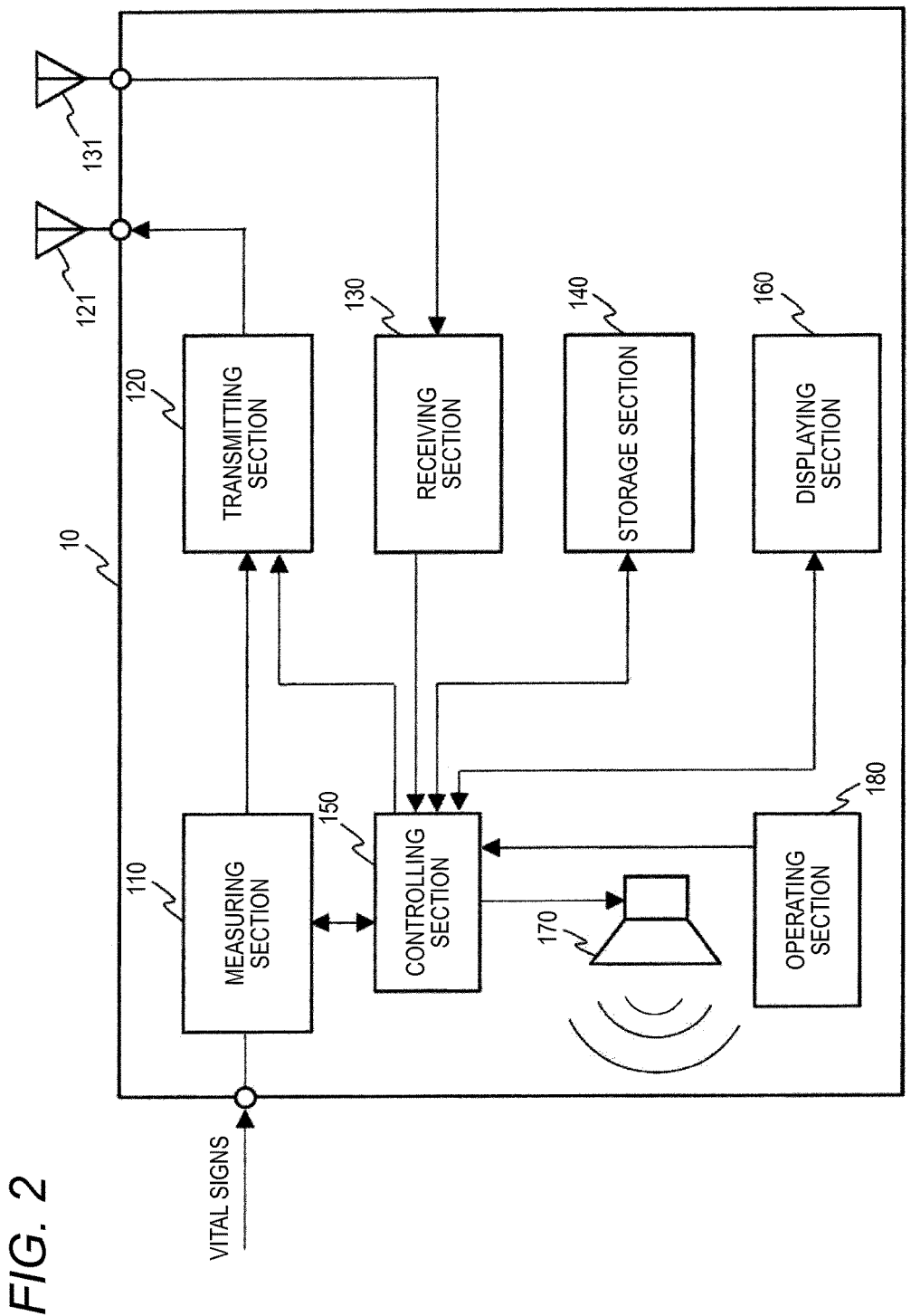
FIG. 2 is a block diagram showing the configuration of a vital signs measuring apparatus 10 of Embodiment 1.

Hereinafter, an embodiment of the presently disclosed subject matter will be described with reference to the drawings. FIG. 1 is a diagram showing the configuration of a vital signs measuring system 1 of Embodiment 1. FIG. 2 is a block diagram showing the internal configuration of a vital signs measuring apparatus 10 constituting the vital signs measuring system 1.

Firstly referring to FIG. 1, as illustrated, the vital signs measuring system 1 includes the vital signs measuring apparatus 10 and a vital signs measuring apparatus 20. Although FIG. 1 shows the two vital signs measuring apparatuses (10, 20), the number of apparatuses is not limited to this, and a configuration where three or more vital signs measuring apparatuses exist may be employed.

For example, the vital signs measuring apparatus 20 is a defibrillator, and measures vital signs of the subject (patient). The vital signs are data such as an electrocardiogram (ECG), the heart rate, the blood pressure, the body temperature, the arterial oxygen saturation, the cardiac output, and the pulse rate. The vital signs measuring apparatus 20 is requested to measure a part of or the whole of these vital signs (an electrocardiogram and the like), and may be a transport monitor, a bedside monitor, or the like.

The vital signs measuring apparatus 20 has a function of transmitting and receiving vital signs (for example, a communication function due to infrared rays or Bluetooth (registered trademark)), and transmits the measured vital signs to the vital signs measuring apparatus 10. Namely, the vital signs measuring apparatus 20 operates as a source measuring apparatus which measures vital signs of the subject, and which transmits the measured data to the vital signs measuring apparatus 10.

The vital signs measuring apparatus 10 receives the vital signs of the subject from the vital signs measuring apparatus 20, and measures and displays vital signs of the subject. For example, the vital signs measuring apparatus 10 is a bedside monitor, and measures various vital signs of the patient (such as an electrocardiogram (ECG), the heart rate, the blood pressure, the body temperature, and the arterial oxygen saturation). In the embodiment, it is assumed that the connection with the subject is switched from the vital signs measuring apparatus 20 to the vital signs measuring apparatus 10. In an ambulance, for example, vital signs of the subject are measured by the defibrillator (vital signs measuring apparatus 20), and, after the ambulance reaches a hospital, the connection with the subject is switched from the defibrillator (vital signs measuring apparatus 20) to the vital signs monitor (vital signs measuring apparatus 10).

Hereinafter, the configuration of the vital signs measuring apparatus 10 will be described in detail with reference to FIG. 2. The vital signs measuring apparatus 10 includes a measuring section 110, a transmitting section 120, a transmission antenna 121, a receiving section 130, a reception antenna 131, a storage section 140, a controlling section 150, a displaying section 160, a speaker 170, and an operating section 180.

The measuring section 110 measures various vital signs through electrodes, transducers, probes, and the like (not shown) which are attached to the subject. As described above, the vital signs relate to an electrocardiogram (ECG), the heart rate, the blood pressure, the body temperature, the arterial oxygen saturation, and the like. The measuring section 110 supplies the acquired various vital signs to the controlling section 150 and the transmitting section 120. It is assumed that the measuring section 110 includes also various filters, A/D (Analog/Digital) converters, and the like.

Under the control of the controlling section 150, the transmitting section 120 transmits the vital signs of the subject to another apparatus through the transmission antenna 121.

The receiving section 130 receives various data (including the vital signs transmitted from the above-described vital signs measuring apparatus 20) from other apparatuses through the reception antenna 131, and supplies the received data to the controlling section 150. Although the description has been made assuming that the configuration of FIG. 2 has both the transmission antenna 121 and the reception antenna 131, a configuration in which a single antenna having a transmission/reception function is disposed may be employed.

The storage section 140 is a storage device which is disposed in the vital signs measuring apparatus 10, and includes, for example, a hard disk drive and various memories. The storage section 140 is not limited to a device incorporated in the vital signs measuring apparatus 10, and may be a device (for example, a USB (Universal Serial Bus) memory) which is detachable from the vital signs measuring apparatus 10.

The controlling section 150 adequately reads operation programs from the storage section 140 to execute them. The controlling section 150 controls the various processing sections in the vital signs measuring apparatus 10. For example, the controlling section 150 analyzes the vital signs acquired by, for example, the measuring section 110, and performs, alarm sounding and displaying controls of various alarms (upper and lower limit alarms, an arrhythmia alarm, and a technical alarm).

The displaying section 160 is a displaying device disposed on the case of the vital signs measuring apparatus 10, and configured by, for example, a liquid crystal display panel and a control circuit for the display panel. The displaying section 160 displays waveforms and numerical data of the vital signs on the display screen. The display screen to be displayed on the displaying section 160 is controlled (produced) by the controlling section 150. When the display screen of vital signs is to be produced, the controlling section 150 changes the display effect in accordance with whether vital signs acquired by another apparatus are to be displayed or not (in other words, whether the data to be displayed are vital signs received by the receiving section 130 or not). An example of the display control by the controlling section 150 will be described later with reference to FIG. 4 and the like.

The speaker 170 outputs various alarms and the like under the control of the controlling section 150.

The operating section 180 is configured by various inputting devices which receive an input by the user. For example, the operating section 180 is configured by buttons, knobs, and the like which are disposed on the case of the vital signs measuring apparatus 10. As in a touch panel, the operating section 180 may be integrated with the displaying section 160.

Figure 3:
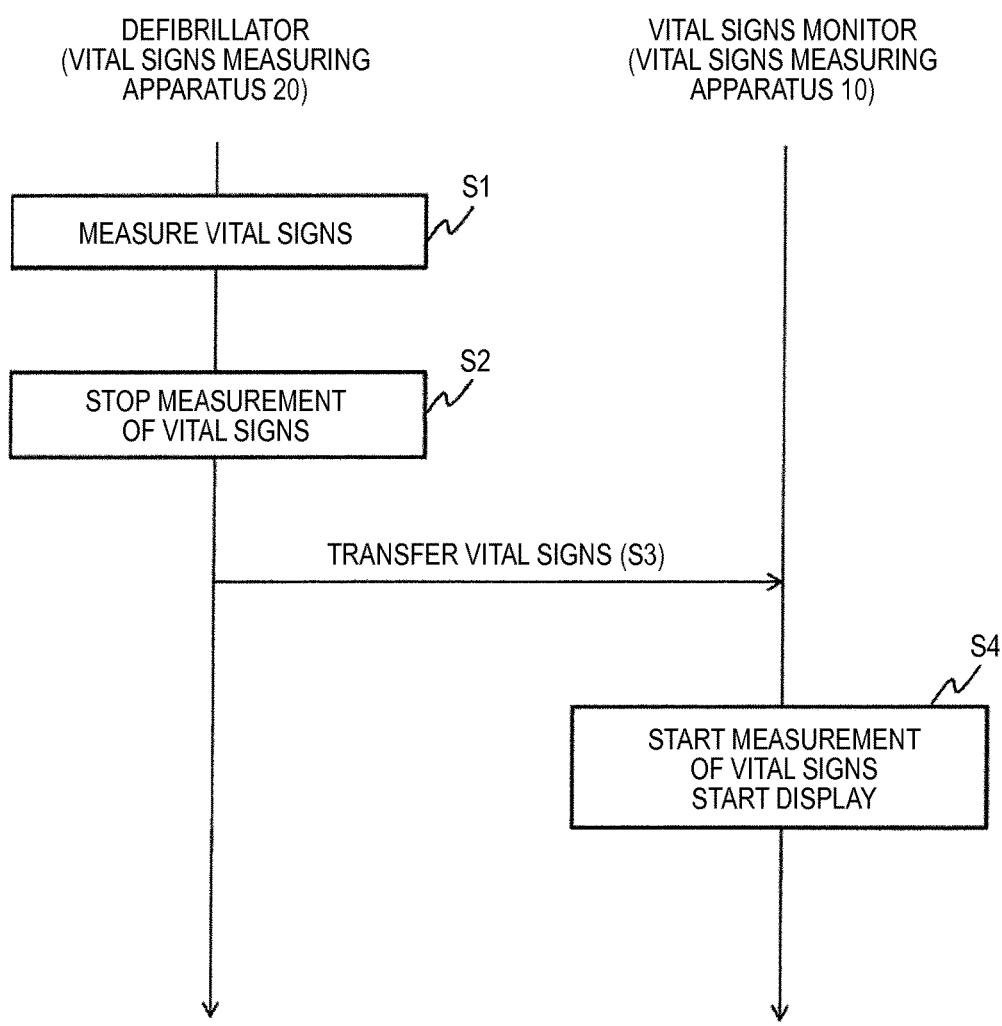
FIG. 3 is a timing chart showing the operational flow of the vital signs measuring system 1 of Embodiment 1.

Referring to FIG. 3, then, the operation flow of the vital signs measuring system 1 will be described. In FIG. 3, the vital signs measuring apparatus 10 is a vital signs monitor (bedside monitor), and the vital signs measuring apparatus 20 is a defibrillator. Firstly, the defibrillator (vital signs measuring apparatus 20) is connected to the subject through the electrodes. The defibrillator (vital signs measuring apparatus 20) measures vital signs of the subject, and stores the measured vital signs (S1). Then, the defibrillator (vital signs measuring apparatus 20) stops the measurement process in response to an operation (for example, an operation performed on a button or the like) by the user (S2). Alternatively, the defibrillator (vital signs measuring apparatus 20) may automatically detect electrode disengagement and the like, and then stop the measurement process (S2).

The defibrillator (vital signs measuring apparatus 20) transfers the measured vital signs to the vital signs monitor (vital signs measuring apparatus 10) (S3). The vital signs monitor (vital signs measuring apparatus 10) receives the vital signs transmitted from the defibrillator (vital signs measuring apparatus 20) (S3). An authentication process may be performed before the transmission and reception of vital signs. The user detaches the electrodes and the like of the defibrillator (vital signs measuring apparatus 20) from the subject, and sets a state where the subject and the vital signs monitor (vital signs measuring apparatus 10) are connected to each other. Thereafter, the vital signs monitor (vital signs measuring apparatus 10) starts measurement of vital signs of the subject (S4). In addition, the vital signs monitor (vital signs measuring apparatus 10) performs a process of displaying vital signs (S4).

A specific example of the display will be described with reference to FIG. 4. As described above, vital signs are supplied from the defibrillator (vital signs measuring apparatus 20) to the vital signs monitor (vital signs measuring apparatus 10). The controlling section 150 in the vital signs measuring apparatus 10 stores the vital signs in the storage section 140 in such a manner that the situation where the vital signs are received from the receiving section 130 can be known (for example, the vital signs are stored while setting a flag). Furthermore, the controlling section 150 stores the vital signs measured by the measuring section 110 in the storage section 140.

The controlling section 150 adequately reads vital signs from the storage section 140, and produces a display screen which is to be displayed on the displaying section 160. In this case, the controlling section 150 causes the vital signs to be displayed while changing the display effect on the display screen based on whether the vital signs are those received by the receiving section 130 or not. As shown in FIG. 4, for example, the controlling section 150 produces a display screen in which the background color of waveforms 40 indicating the vital signs received from the defibrillator (vital signs measuring apparatus 20) is different from that of waveforms 41 indicating the vital signs measured by the measuring section 110. Furthermore, the controlling section 150 may display measurement values (numerical values) of the vital signs corresponding to the waveforms (40, 41) while changing the background colors of the measurement values.

When the user views the display screen, the user can easily know not only the measurement values of the vital signs, but also the measurement conditions under which the measurement values have been acquired. That is, the user can know that the waveforms 40 provided with the different background color indicate vital signs measured by another apparatus.

Figure 4:
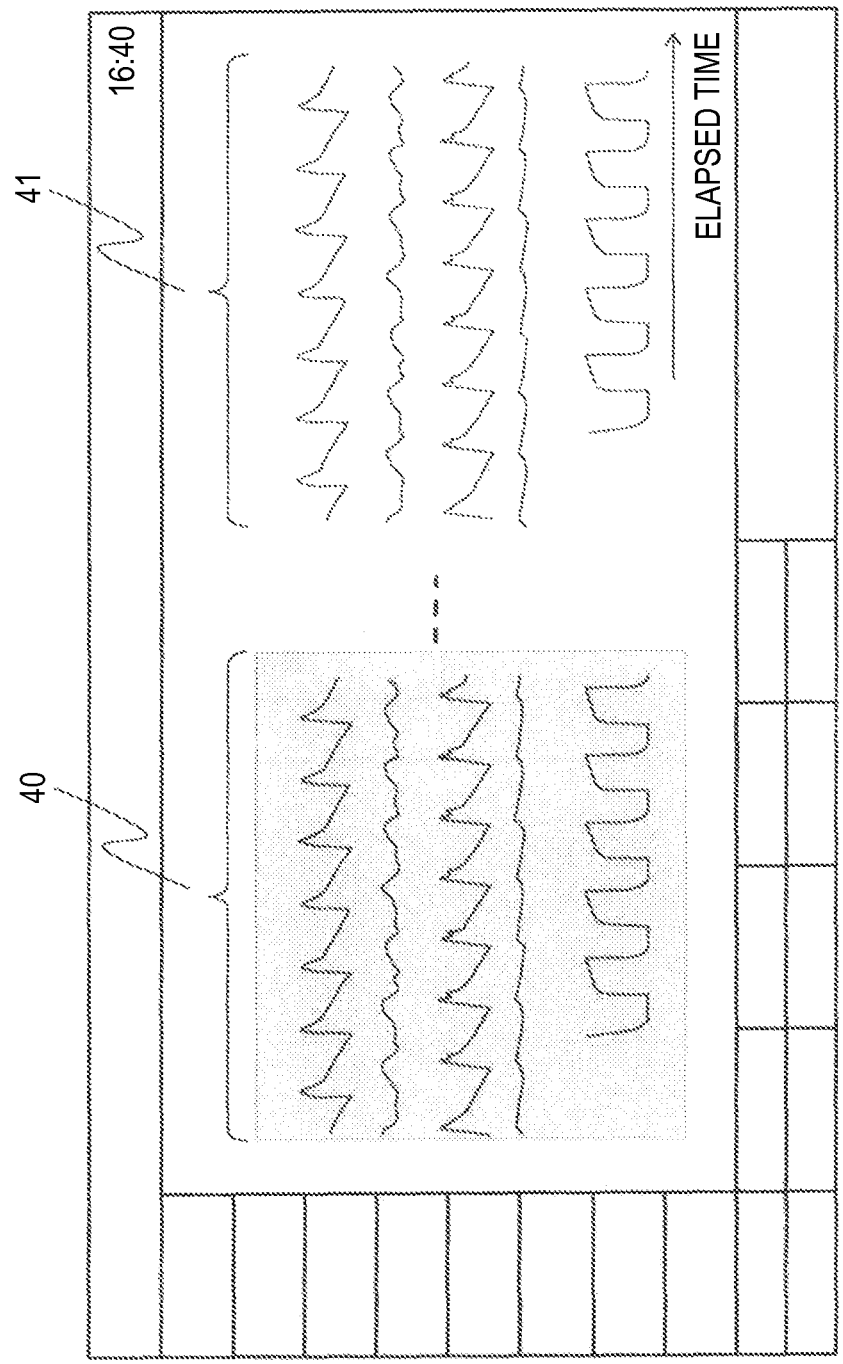
FIG. 4 is a conceptual view showing an example of a display screen in Embodiment 1.

The configuration where the background colors are changed as in FIG. 4 is an example of the change of the display effect. Configurations where the display effect is changed in another mode may be employed. For example, the controlling section 150 may change the line types (a broken line, a dash-dot line, a thick line, and the like) or colors of waveforms in accordance with whether the vital signs are those received by the receiving section 130 or not. Other kinds of the display effect such as that only one waveform is blinked, and that the sets of waveforms (the waveforms 40 and the waveforms 41) are surrounded by frames of different colors, respectively may be employed.

Then, effects of the vital signs measuring system 1 and vital signs measuring apparatus 10 of the embodiment will be described. In the measurement conditions of the vital signs measuring apparatus, the kind of an apparatus which performed the measurement is an important condition. Some apparatuses are often used while moving. The measurement accuracy varies depending on whether the apparatus is of a sophisticated type or of a general-purpose type. Therefore, it is preferable for the user that the information of the apparatus which has measured the vital signs can be referred together the vital signs.

As described above, the vital signs measuring apparatus 10 has the configuration where vital signs of the subject are measured, and vital signs of the subject are received from the other apparatus (vital signs measuring apparatus 20). The controlling section 150 in the vital signs measuring apparatus 10 changes the display effect of vital signs on the display screen based on whether the vital signs are those measured by the own apparatus or not (in other words, whether the vital signs are those received by the receiving section 130 or not) (for example, FIG. 4). That is, the controlling section 150 changes the display effect of vital signs in accordance with the apparatus which has measured the vital signs. Therefore, the user can know measurement values and waveforms of the vital signs, and also the measurement conditions (in the embodiment, whether the data have been measured by another apparatus or not) under which the measurement has been performed. With respect to vital signs which are measured in a situation where the apparatus is largely shaken, for example, the vital signs are requested to be referred on the premise that much noise existed. Therefore, the condition of the subject can be acquired more correctly.

In the case where the background color is changed as shown in FIG. 4, particularly, the user can immediately know the measurement environment (apparatus). Therefore, it is possible to know correctly and quickly the condition of the subject.

(Modification)

Figure 5:
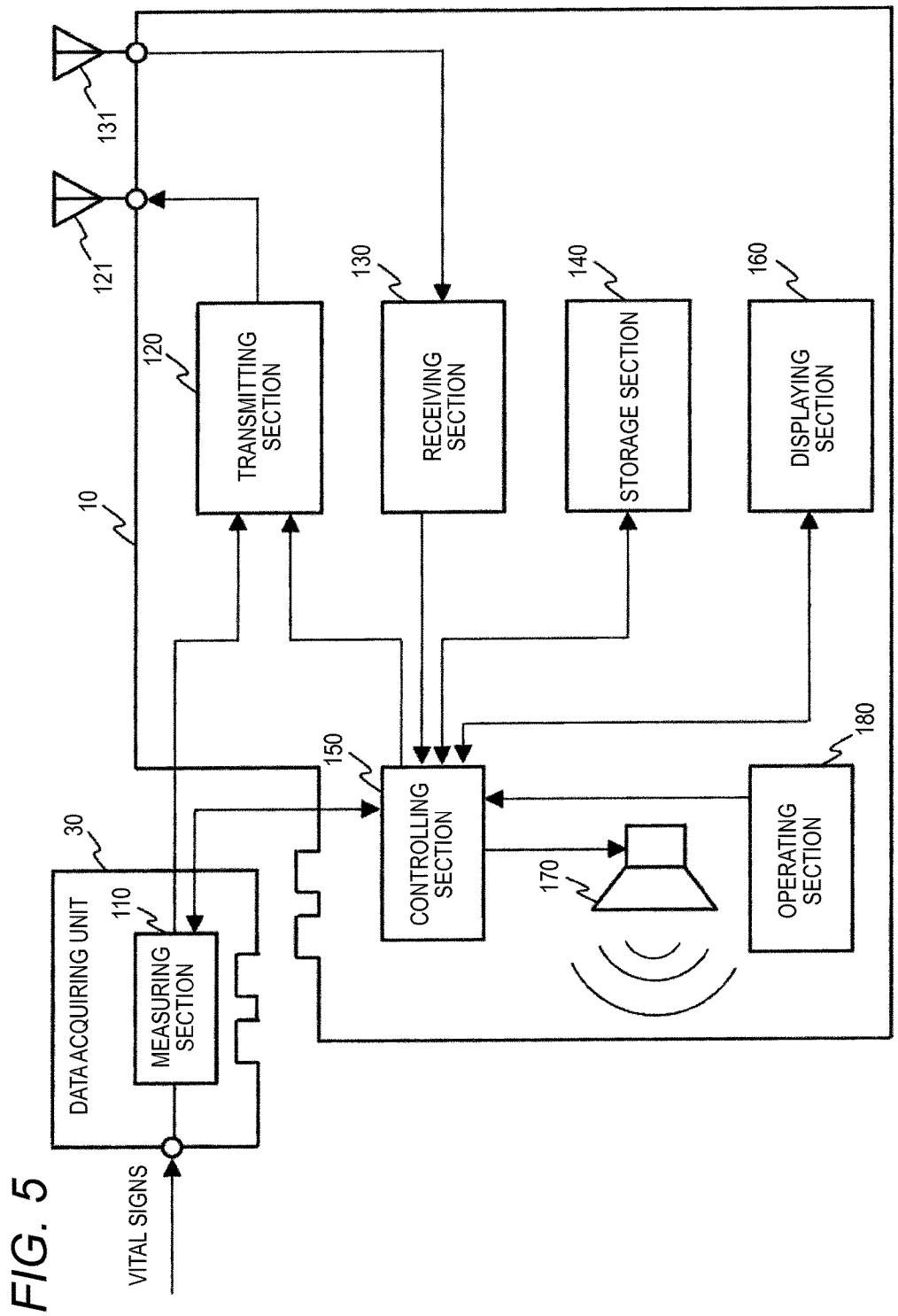
FIG. 5 is a block diagram showing the configuration of the vital signs measuring apparatus 10 of Embodiment 1.

A modification of Embodiment 1 will be described with reference to FIG. 5. The vital signs measuring apparatus 10 is configured so that a data acquiring unit 30 including the measuring section 110 is detachably disposed. The data acquiring unit 30 has a CPU, memory, and the like which are not shown, and acquires vital signs of the subject through electrodes, sensors, and the like which are not shown. When the data acquiring unit 30 is attached to the vital signs measuring apparatus 10, the unit supplies the acquired vital signs to the controlling section 150.

The controlling section 150 may provide vital signs which are acquired in the state where the data acquiring unit 30 is detached from the vital signs measuring apparatus 10, with a display effect which is similar to that provided to vital signs acquired from the receiving section 130 (namely, vital signs which are acquired in the state where the data acquiring unit 30 is detached from the vital signs measuring apparatus 10 may be treated as those received from the receiving section 130). For example, the controlling section 150 may determine the display effect in the following manners:

Vital signs acquired in the state where the data acquiring unit 30 is detached: (background color=gray), Vital signs acquired in the state where the data acquiring unit 30 is connected: (background color=black), and Vital signs acquired through the receiving section 130: (background color=gray).

The above-described coloration is a mere example. With respect to vital signs acquired by the data acquiring unit 30, the display effect may be determined irrespective of the attachment/detachment state in the following manners:

Vital signs acquired in the state where the data acquiring unit 30 is detached: (background color=black), Vital signs acquired in the state where the data acquiring unit 30 is connected: (background color=black), and Vital signs acquired through the receiving section 130: (background color=gray).

Alternatively, the display effect may be changed in each of the above three states:

Vital signs acquired in the state where the data acquiring unit 30 is detached: (background color=gray), Vital signs acquired in the state where the data acquiring unit 30 is connected: (background color=black), and Vital signs acquired through the receiving section 130: (background color=deep blue).

The color setting may be determined in accordance with a mode setting performed by the user. It is a matter of course that, in place of setting of the background color, other display effects (for example, the kind of the line of a waveform is changed, the thickness of a waveform is changed, or waveforms are surrounded by frames of different colors) may be employed.

Embodiment 2

With respect to the configuration of the vital signs measuring system 1 of Embodiment 2, then, points which are different from Embodiment 1 will be described. The embodiment is characterized in that the controlling section 150 in the vital signs measuring apparatus 10 changes the display effect in consideration of attribute data transmitted from the vital signs measuring apparatus 20.

The configuration of the vital signs measuring system 1 is similar to that shown in FIG. 1. In the embodiment, however, the vital signs measuring apparatus 20 transmits attribute data which will be described later, together with vital signs.

The internal configuration of the vital signs measuring apparatus 10 is similar to that shown in FIG. 2. In the embodiment, however, the controlling section 150 changes the display effect in consideration of the attribute data.

Firstly, an example of the attribute data will be described with reference to FIG. 6. The attribute data indicate various attributes of the vital signs measuring apparatus 20 (source measuring apparatus) (for example, the use of the apparatus, the apparatus ID, and the type of the apparatus). In FIG. 6, for example, "transportation" indicating that the apparatus is a monitor for transportation is described as the use of the apparatus. The vital signs measuring apparatus 20 transmits the attribute data (FIG. 6) together with vital signs to the vital signs measuring apparatus 10. The data format of the attribute data shown in FIG. 6 is a mere example. An arbitrary data format (the CSV type or the like) may be employed. Attribute data may be similarly defined with respect to the own apparatus. That is, attribute data indicating the use, type No., and the like of the vital signs measuring apparatus 10 may be defined in the storage section 140 in the vital signs measuring apparatus 10.

The receiving section 130 in the vital signs measuring apparatus 10 receives the attribute data (FIG. 6) together with the vital signs. The controlling section 150 stores the vital signs and attribute data (FIG. 6) which are received, in the storage section 140 in association with one another. The controlling section 150 reads the vital signs and the attribute data (FIG. 6), and changes the display effect of the vital signs on the display screen in accordance with the attribute data.

For example, it is assumed that correlation tables such as shown FIGS. 7A and 7B are defined in the storage section 140. Referring to the correlation table (FIG. 7A or 7B), the controlling section 150 produces a display screen displaying the vital signs. FIG. 7A shows an example of a correlation table produced in the case where the display effect is determined in considering whether the reception process of the receiving section 130 is performed or not, and "Use" of the attribute data (FIG. 6). With respect to vital signs which are received by the receiving section 130, and in which "transportation" is defined as attribute data, for example, waveforms are displayed on the display screen while setting the background color to gray.

FIG. 7B shows an example of a correlation table produced in the case where the display effect is determined in consideration of only the attribute data (FIG. 6). For example, the background color of waveforms of vital signs measured by an apparatus in which the use is "transportation" is gray, and that of waveforms of vital signs measured by the own apparatus (measuring section 110) is deep blue.

Although, in the examples of FIGS. 7A and 7B, the display effect is defined according to the use ("Use" tag of the attribute data) of each apparatus, the presently disclosed subject matter is not limited to this. For example, correspondence relationships of apparatus IDs and display effects may be defined, or correspondence relationships of type numbers of apparatuses and display effects may be defined. The correlation tables (FIGS. 7A and 7B) may be changed by the user through a setting screen.

The display screen is similar to the example shown in FIG. 4, and therefore its detailed description is omitted.

Then, effects of the vital signs measuring system 1 and vital signs measuring apparatus 10 of the embodiment will be described. In the embodiment, the controlling section 150 changes the display effect of vital signs on the display screen based on attribute data (the apparatus ID, the use of the apparatus, the type of the apparatus, and the like). In the case where the use of the apparatus is an environment in which noise is easily imposed on vital signs, such as the use in transportation purpose or that in an ambulance, the background of display waveforms of vital signs is displayed in a color which is different from the usual one. According to the configuration, the user can refer to a change of the vital signs while knowing more detailed measurement conditions.

Embodiment 3

With respect to the configuration of the vital signs measuring apparatus 10 of Embodiment 3, then, points which are different from Embodiments 1 and 2 will be described. In the embodiment, the vital signs measuring apparatus 10 handles vibration generated during measurement of vital signs, as the measurement conditions. That is, the embodiment is characterized in that the vital signs measuring apparatus 10 detects vibration generated during measurement of vital signs, and changes the display effect in accordance with the degree of the vibration.

Figure 8:
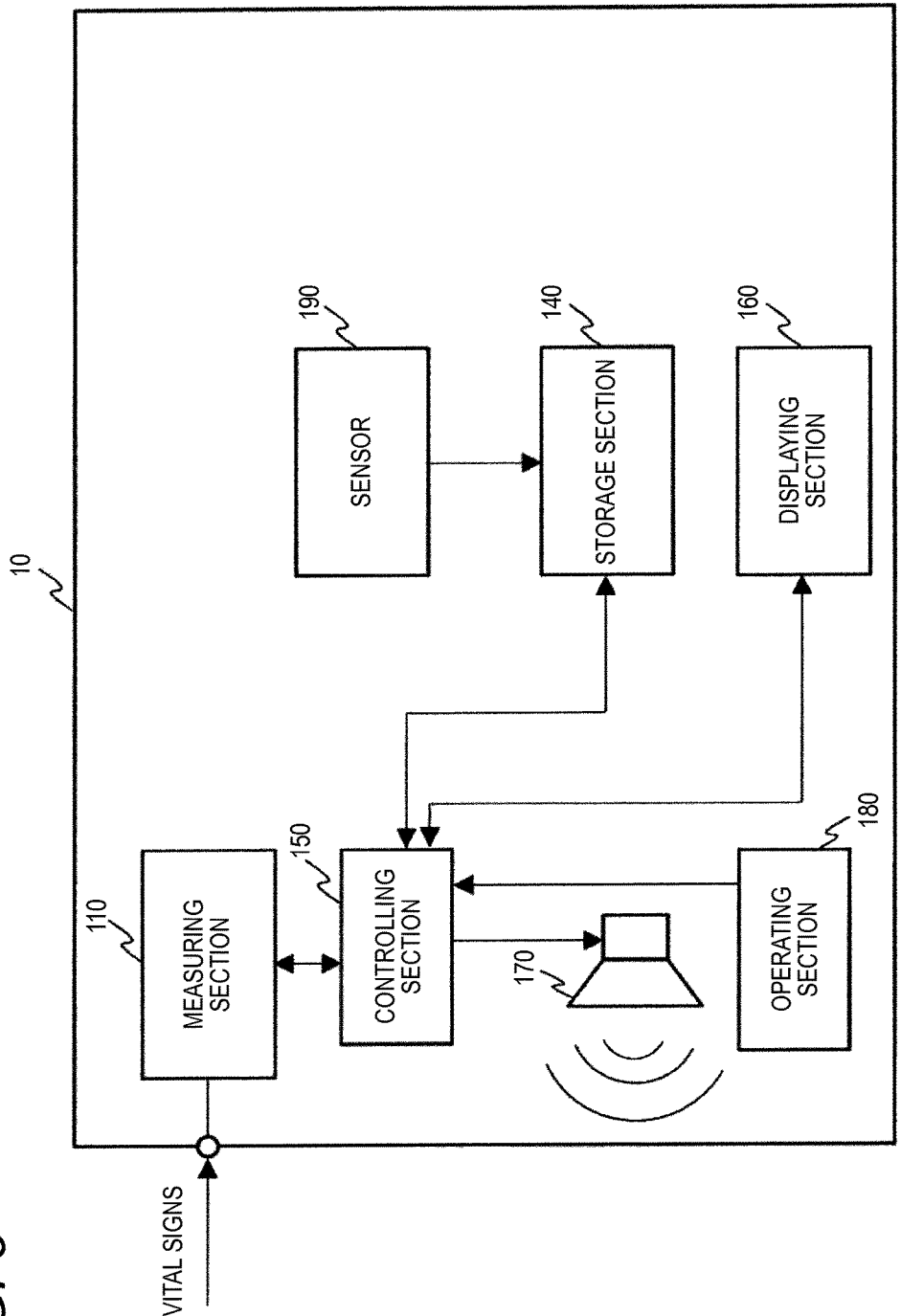
FIG. 8 is a block diagram showing the configuration of a vital signs measuring apparatus 10 of Embodiment 3.

FIG. 8 is a block diagram showing the configuration of the vital signs measuring apparatus 10 of the embodiment. The vital signs measuring apparatus 10 of the embodiment has a configuration where the apparatus has a sensor 190. The vital signs measuring apparatus 10 may be configured so as not to have the processing sections related communication (the transmitting section 120, the transmission antenna 121, the receiving section 130, and the reception antenna 131) as illustrated, or so as to have the processing sections related communication similarly with FIG. 2.

The sensor 190 is a device which detects the degree of vibration generated in the vital signs measuring apparatus 10. For example, the sensor 190 may be an acceleration sensor, a piezoelectric vibration sensor, or the like. During measurement of vital signs by the measuring section 110, the sensor 190 measures data (vibration data) indicating the degree of vibration, and stores the data in the storage section 140.

Figure 9:
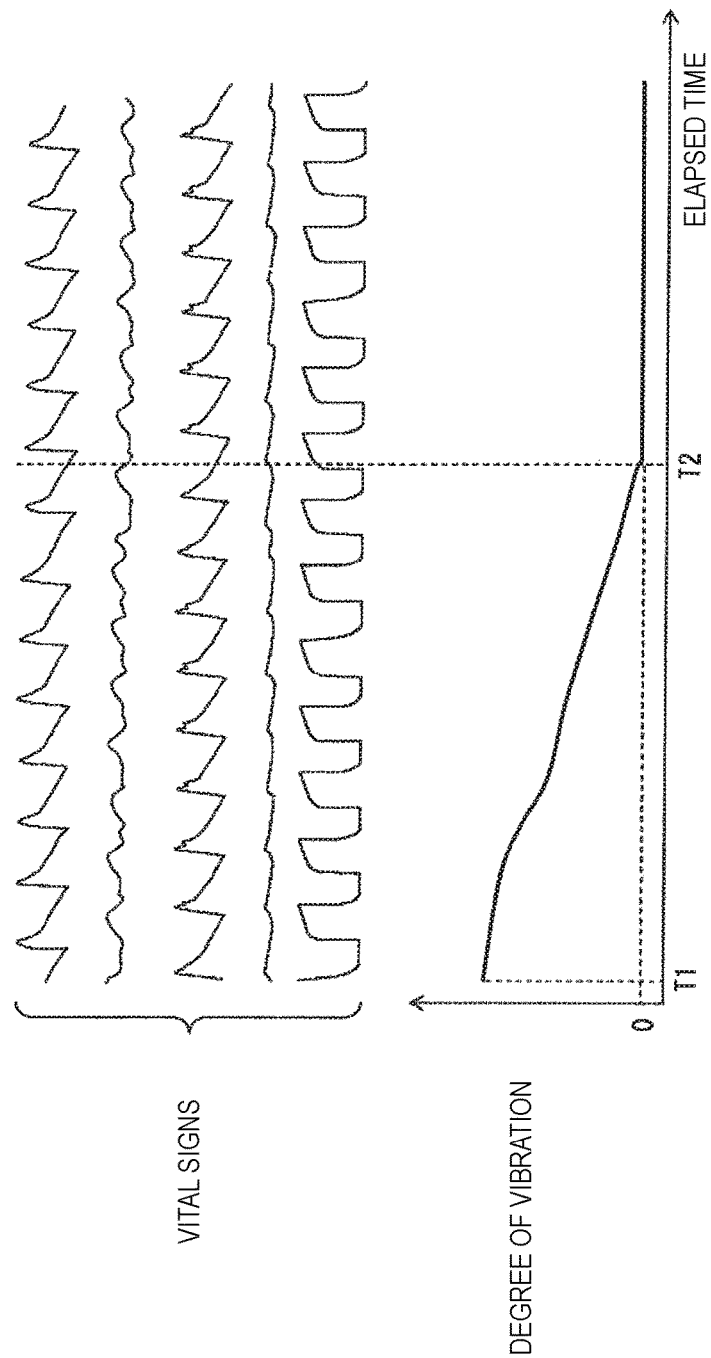
FIG. 9 is a view showing relationships between vibration data and vital signs in Embodiment 3.

FIG. 9 is a view showing relationships between the vibration data measured by the sensor 190, and vital signs measured by the measuring section 110. From the figure, it is seen that vibration occurs in a time period between times T1 and T2, and no vibration is generated after time T2.

Figure 10:
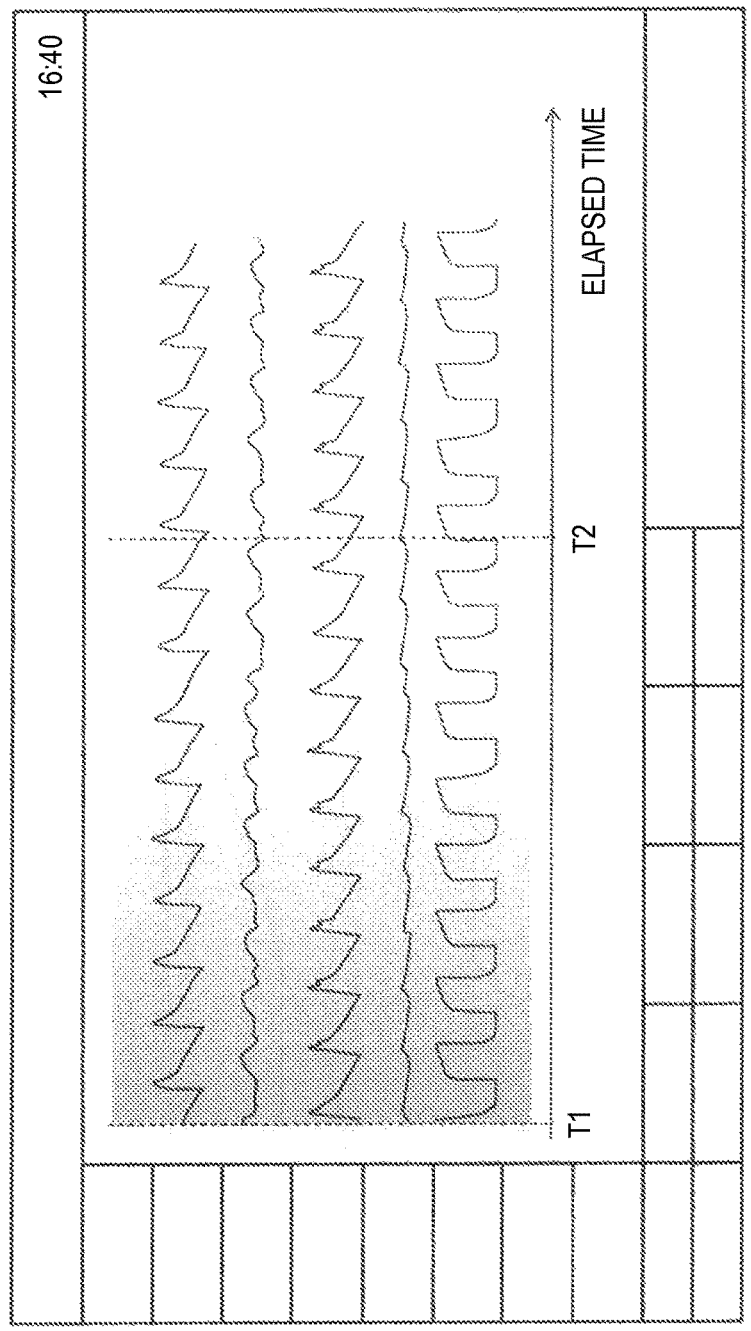
FIG. 10 is a conceptual view showing an example of a display screen in Embodiment 3.

The controlling section 150 produces the display screen to be produced on the displaying section 160, by using the data (the vibration data and the vital signs) shown in FIG. 9. The controlling section 150 changes the display effect of the vital signs on the display screen in accordance with the degree of vibration. For example, the controlling section 150 changes the density of the background color of waveforms indicating vital signs as shown in FIG. 10. In the example of FIG. 10, in the case where large vibration is generated, the display screen is produced so that the density of the background color becomes higher. In place of the change of the density of a monochrome as illustrated, the background color may be gradationally changed in accordance with the degree of vibration.

Then, effects of the vital signs measuring apparatus 10 of the embodiment will be described. As described above, the vital signs measuring apparatus 10 detects the degree of vibration generated during measurement of vital signs, and changes the display effect of the vital signs on the display screen in accordance with the degree of the vibration. When referring to the display screen (FIG. 10), the user can know not only the waveforms and measurement values of vital signs, but also the degree of vibration produced during the measurement.

Since the degree of vibration is acquired as numerical data, it is possible also to finely change the density of the background color in accordance with the change of the degree (numerical data) of the vibration as shown in FIG. 10 (it is possible also to gradationally change the background color). When referring to the display screen (FIG. 10), the user can immediately know a subtle change of the degree of vibration, and more correct diagnosis can be given to the patient.

It is a matter of course that another display effect such as that in which, in place of the background color, the type, width, and the like of the line indicating a waveform are changed may be employed.

Although the presently disclosed subject matter conducted by the inventor has been specifically described based on the embodiments, the presently disclosed subject matter is not limited to the above-described embodiments, and it is a matter of course that various changes can be made without departing from the spirit of the presently disclosed subject matter.

The processes of the controlling section 150 may be realized as computer programs which operate in vital signs measuring apparatus 10. The programs may be stored in a non-transitory computer readable medium of any one of various types, and then supplied to the computer. The non-transitory computer readable medium includes tangible storage media of various types. Examples of the non-transitory computer readable medium are a magnetic recording medium (for example, a flexible disk, a magnetic tape, and a hard disk drive), a magneto-optical recording medium (for example, a magneto-optical disk), a CD-ROM (Read Only Memory), a CD-R, a CD-R/W, a semiconductor memory (for example, a mask ROM, a PROM (Programmable ROM), an EPROM (Erasable PROM), a flash ROM, and a RAM (Random Access Memory)). Alternatively, the programs may be supplied to the computer by means of a transitory computer readable medium of any one of various types. Examples of the transitory computer readable medium are an electrical signal, an optical signal, and an electromagnetic wave. The transitory computer readable medium can supply the programs to the computer through a wired communication path such as a metal wire or an optical fiber, or a wireless communication path.

According to an aspect of the presently disclosed subject matter, the controlling section changes the display effect of vital signs based on whether the vital signs are those received by the receiving section or not. Namely, the controlling section changes the display effect of vital signs in accordance with the apparatus which has measured the data. Therefore, the user can know measurement values and waveforms of the vital signs, and also the measurement conditions under which the measurement has been performed, and can acquire more correctly the condition of the subject.

The presently disclosed subject matter can provide a vital signs measuring apparatus, vital signs displaying method, and program in which vital signs can be referred after recognizing measurement conditions.

What is claimed is:

1. A vital sign measuring apparatus comprising:
at least one processor and memory configured to:
measure a vital sign of a subject;
receive the vital sign of the subject, wherein the received vital sign is measured by a second vital sign measuring apparatus and is transmitted from the second vital sign measuring apparatus to the vital sign measuring apparatus; and
produce a display screen that changes a display effect of the vital sign on the display screen based on whether the vital sign on the display screen is the vital sign received from the second vital sign measuring apparatus, such that a display effect of the received vital sign is different from a display effect of the measured vital sign; and
a display configured to display the display screen and at least one of the measured vital sign and the received vital sign,
wherein the vital sign measured by the vital sign measuring apparatus and the vital sign received from the second vital sign measuring apparatus are the same vital sign, and the second vital sign measuring apparatus is separate from the vital sign measuring apparatus.

2. The vital signs measuring apparatus according to claim 1, wherein the at least one processor and memory are further configured to change a background color of a waveform or a measurement value of vital signs based on whether the vital sign is received by the vital sign measuring apparatus.

3. The vital signs measuring apparatus according to claim 1, wherein the at least one processor and memory are further configured to:
attribute data indicating an attribute of the second vital sign measuring apparatus, and
based on whether vital signs are received and contents of the attribute data, change a display effect of the vital signs on the display screen.

4. The vital signs measuring apparatus according to claim 3, wherein the attribute data contain information of at least one of a use of the second vital sign measuring apparatus, an ID of the second vital sign measuring apparatus, and a type of the second vital sign measuring apparatus.

5. The vital signs measuring apparatus according to claim 1, wherein the at least one processor and memory configured to measure vital signs are disposed in a data acquiring unit that is attachable to and detachable from a case housing the display.

6. The vital signs measuring apparatus according to claim 1, wherein the display effect is a line type of a waveform of the vital sign on the display screen.

7. The vital signs measuring apparatus according to claim 1, wherein the display effect is a color of a waveform of the vital sign on the display screen.

8. The vital signs measuring apparatus according to claim 1, wherein the measured vital sign and the received vital are both displayed according to a time series.

9. The vital signs measuring apparatus according to claim 1, wherein the at least one processor and memory are further configured to:
separately store data corresponding to the measured vital sign from data corresponding to the received vital sign;
read the stored data corresponding to the measured vital sign, and the stored data corresponding to the received vital sign; and
produce the display screen based on the read data corresponding to the measured vital sign, and the read data corresponding to the received vital sign.

10. A vital sign measuring apparatus comprising:
at least one processor and memory configured to:
measure a vital sign of a subject;
receive, from a second vital sign measuring apparatus, the vital sign of the subject as measured by the second vital sign measuring apparatus and attribute data indicating an attribute of the second vital sign measuring apparatus;
store a table indicating relationships between display effects and contents of the attribute data; and
produce a display screen that changes a display effect of the vital sign on the display screen based on the contents of the attribute data; and
a display configured to display at least one of the measured vital sign and the received vital sign,
wherein the vital sign measured by the vital sign measuring apparatus and the vital sign received from the second vital sign measuring apparatus are the same vital sign, and the second vital sign measuring apparatus is separate from the vital sign measuring apparatus.

11. A vital signs measuring apparatus comprising:
at least one processor and memory configured to:
measure vital signs of a subject over a period of time;
in conjunction with a sensor, detect a degree of vibration generated in the vital signs measuring apparatus when measuring the vital signs of the subject over the period of time; and
produce a display screen that, for each instantaneous time within the period of time, illustrates the vital signs on the display screen at the instantaneous time, and a display effect based on the degree of vibration detected by the sensor at the instantaneous time, such that the vital signs and degree of vibration as illustrated by the display effect are correlated on the display screen for each instantaneous time; and
a display configured to display the measured vital signs and display effect of the display screen.

12. The vital signs measuring apparatus according to claim 11, wherein the at least one processor and memory are further configured to change a density of a background color of a display area for a waveform indicating the vital signs based on the degree of vibration detected by the sensor.

13. A vital signs displaying method comprising:
measuring a vital sign of a subject at a first vital sign measuring apparatus;
receive the vital sign of the subject, wherein the received vital sign is measured by a second vital sign measuring apparatus and is transmitted from the second vital sign measuring apparatus to the first vital sign measuring apparatus;
displaying at least one of the measured vital sign and the received vital sign; and
producing a display screen that is to be displayed, and changing a display effect of the vital sign on the display screen based on whether the vital sign on the display screen is the received vital sign, such that a display effect of the received vital sign from the second vital sign measuring apparatus is different from a display effect of the measured vital sign from the first vital sign measuring apparatus,
wherein the vital sign measured by the first vital sign measuring apparatus and the vital sign received from the second vital sign measuring apparatus are the same vital sign, and the second vital sign measuring apparatus is separate from the first vital sign measuring apparatus.

14. A non-transitory computer-readable recording medium storing a program causing a computer to execute the method according to claim 13.

15. A vital sign measuring apparatus comprising:
at least one processor and memory configured to:
measure a vital sign of a subject;
receive the vital sign of the subject, wherein the received vital sign is measured by a second vital sign measuring apparatus and is transmitted from the second vital sign measuring apparatus to the vital sign measuring apparatus; and
produce a display screen of the vital sign that changes a color based on a user selected mode and whether the vital sign on the display screen is the vital sign received from the second vital sign measuring apparatus, such that a color of the received vital sign is different from a color of the measured vital sign; and
a display configured to display the display screen and at least one of the measured vital sign and the received vital sign,
wherein the vital sign measured by the vital sign measuring apparatus and the vital sign received from the second vital sign measuring apparatus are the same vital sign, and the second vital sign measuring apparatus is separate from the first vital sign measuring apparatus.

* * * * *